US00PP14126P39

(12) United States Plant Patent
Zaiger et al.

(10) Patent No.: US PP14,126 P3
(45) Date of Patent: Sep. 2, 2003

(54) SELECT MYROBALAN TREE 'RI-1'

(76) Inventors: Chris Floyd Zaiger, 929 Grimes Ave., Modesto, CA (US) 95358; Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 09/814,582

(22) Filed: Mar. 21, 2001

(65) Prior Publication Data

US 2002/0138884 P1 Sep. 26, 2002

(51) Int. Cl.[7] ..... A01H 5/00
(52) U.S. Cl. ..... Plt./183
(58) Field of Search ..... Plt./180, 183, 181, Plt./182

(56) References Cited

PUBLICATIONS

L.H. Bailey, 'The Standard Cyclopedia of Horticulture', 1935, Macmillan and Co., p. 2825.*

* cited by examiner

*Primary Examiner*—Bruce R. Campell
*Assistant Examiner*—Susan B. McCormick
(74) *Attorney, Agent, or Firm*—Stratton Ballew PLLC

(57) ABSTRACT

A new and distinct variety of Myrobalan tree (*Prunus cerasifera*). Its novelty consists of the following unique combination of features that are desirable in a new interstock when growing cherries:

1. Decreasing the height of the cherry tree for more economical harvesting.
2. Providing earlier production of fuit when growing cherries with the new interstock variety on Citation Rootstock.
3. Increasing the number of rootstocks available for cherries.
4. Improving the opportunity to match soil type with the desired rootstock by using an interstock.

1 Drawing Sheet

Latin name: *Prunus cerasifera.*
Variety denomination: RI-1.

BACKGROUND OF THE VARIEETY

In the field of plant genetics, we conduct an extensive and continuing plant-breeding program including the organization and asexual reproduction of orchard trees, and of which plums, peaches, nectarines, apricots, cherries, interspecifics and rootstocks are exemplary. It was against this background of our activities that the present variety of rootstock-interstock was originated and asexually reproduced by us in an experimental orchard located near Modesto, Stanislaus County, Calif.

PRIOR VARIETIES

Among the existing varieties of rootstocks which are known to us, and mentioned herein, are 'Nemaguard' Rootstock (non-patented), 'Atlas Rootstock' (U.S. Plant Pat. No. 8,913), 'Viking ' Rootstock (U.S. Plant Pat. No. 8,912), Citation™ Rootstock (U.S. Plant Pat. No. 5,112), 'Mazzard' Rootstock (non-patented), and 'Mahaleb' Rootstock (non-patented).

ORIGIN OF THE VARIETY

It is well known that sweet cherry trees are compatible with a very limited number of rootstocks for commercial production. For many years, the primary rootstocks available for the production of commercial cherry trees have been 'Mahaleb' (non-patented) and 'Mazzard' (non-patented). Both of these varieties are undesirably tall, and have a long juveninity period, delaying production of fruit for five to seven years. Additionally, 'Mahaleb' is susceptible to phytophthora root rot and over cropping, which results in small fruit size. 'Mazzard' is a stronger tree with lighter production, but is even taller than 'Mahaleb'.

Due to the limitations of the rootstocks presently available for commercial cherry trees, we attempted to identify a new interstock that would be compatible with a variety of commercially available rootstocks, as well as with sweet cherry varieties.

The present new Myrobalan tree (*Prunus cerasifera*) was originated by us in our experimental orchard located near Modesto, Calif. as a selection from seed of open pollinated populations of Myrobalan rootstocks. The exact parentage of the new variety is unknown. We planted and maintained a large group of these open pollinated Myrobalan seedlings growing on their own root system in our experimental orchard. We budded and grafted these seedlings to various rootstocks and various varieties of cherries (*Prunus avium*), searching for an interstock between the various species. We experienced some success with several combinations, but one seedling, now known as 'RI-1', showed particular promise as an interstock. That seedling was tested by budding and grafting and found to be compatible with cherries and several rootstocks, as was thus selected for asexual propagation and commercialization as an interstock for use with cherry scion wood.

'RI-1' is distinguishable from other cultivars of the species by its compatibility with cherry trees. Specifically, the 'RI-1' cultivar, when used as an interstock, exhibits significantly less overgrowth at the union of the interstock and scion, as compared with other known Myrobalan cultivars, and exhibits no overgrowth at the union of the rootstock and interstock. The new interstock is graft compatible with a variety of prunus rootstocks, which allows growers to select the most desirable rootstock for a particular type of soil.

ASEXUAL REPRODUCTION OF THE VARIETY

Asexual reproduction of the new and distinct variety of Myrobalan tree was by budding to Citation™ Rootstock (U.S. Plant Pat. No. 5,112) as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of Myrobalan tree (*Prunus cerasifera*) is of medium size, moderately vigorous, upright in growth and graft compatible with a moderate range of prunus species, which makes it available to be used as an interstock between cherries (*Prunus avium*) and the interspecific rootstock Citation™ (U.S. Plant Pat. No. 5,112) (*Prunus salicina*× *Prunus persica*). Budding and grafting tests show compatibility with the following rootstocks and scions: 'Nemaguard' Rootstock (non-patented), Citation™ Rootstock (U.S. Plant Pat. No. 5,112), 'Viking' Rootstock (U.S. Plant Pat. No. 8,912), 'Atlas' Rootstock (U.S. Plant Pat. No. 8,913), 'Craigs Crimson' Cherry (U.S. Plant Pat. No. 7,320), 'Earlisweet' Cherry (U.S. Plant Pat. No. 9,783), 'Royal Rainier' Cherry (U.S. Plant Pat. No. 10,790) and the following non-patented cherries: 'Bing', 'Van', 'Rainier', 'Black Tartarian', 'Stella', 'Lapins' and 31 seedling selections of cherries in the advanced testing stage. We expect that similar compatibility will be exhibited with other cherry varieties.

Cherries growing on the new Myrobalan interstock grafted to Citation™ rootstock ("Citation-Myrobalan-cherry composite tree") have been observed over a fourteen (14) year period. We have observed a moderate variability in the amount of dwarfing effect within cherry varieties when using the same length of interstock. Decreasing the length of interstock reduces the size of the tree in all cherry varieties, some varieties with a greater degree of dwarfing than other varieties. The interstock should be at least about four inches (approximately 10 cm) in length, and should be no more than about 18 inches (approximately 46 cm) in length. A 6 inch (approximately 15 cm) interstock is preferable. For example, 'Earlisweet' Cherry can be reduced to approximately one-third of normal tree size and 'Rainier' Cherry reduced to approximately one-half normal tree size when budded to a 6-inch segment of the new Myrobalan interstock growing on Citation™ Rootstock. The combination of the new Myrobalan interstock with Citation™ Rootstock has increased precociousness with cherries we have tested to start fruit production in the third year. Crop load is relatively heavy.

The Myrobalan interstock union on the above rootstocks, including Citation™, is relatively smooth, while the bud union on the cherry scion is more prone to be slightly over-grown. The amount of over growth varies within cherry varieties. This same type of overgrowth can be found when growing cherries without an interstock on standard cherry rootstocks such as 'Mahaleb'. We have had no tree loss with the new Myrobalan interstock from breaking at bud union of either cherry or rootstock.

The Citation-Myrobalan-cherry composite tree has been grown in our test orchards and shows promise as commercial fruit tree. Based on our observations of the Citation-Myrobalan-cherry composite tree, we expect that related composite trees will have similar qualities. Such composite trees could include any of the rootstocks named above, or any prunus or interspecific rootstocks that are compatible with the new Myrobalan interstock. The composite trees could further include any of the sweet cherry varieties named above, or any sweet cherry varieties that are compatible with the new Myrobalan interstock.

PHOTOGRAPH OF THE VARIETY

The accompanying color photographic illustration shows typical specimens of the foliage and fruit of the present new Myrobalan variety. The illustration shows the upper and lower surface of the leaves, an exterior and sectional view of a fruit divided in its suture plane to show flesh color, pit cavity and the stone remaining in place. The photographic illustration was taken shortly after being picked and the colors are as true as is reasonably possible in a color representation of this type.

DESCRIPTION OF THE VARIETY

The following detailed botanical description of the new Myrobalan tree, its flowers, foliage and fruit, is based on an exemplary tree, budded on Citation™ Interspecific Rootstock (U.S. Plant Pat. No. 5,112), grown on Handford sandy loam soil with Storie Index rating 95, in USDA Hardiness Zone 9, near Modesto, Calif., with standard commercial fruit growing practices, such as pruning, thinning, spraying, irrigation and fertilization. At the time the description was recorded, the tree was 7 years old. Color terminology (except those in common terms) is in accordance with Reinhold Color Atlas by A. Kornerup and J. H. Wanscher.

Tree:

*Size.*—Medium to large. Tree pruned severely each winter to induce proper new growth for budwood.

*Vigor.*—Moderately vigorous. Tree growth of 5 to 6 feet (1.5 to 1.8 m) in height and 3 to 4 feet (0.9 to 1.2 m) in width the first growing season.

*Growth.*—Upright. Each dormant season tree is cut back to 4 to 6 feet (0.9 to 1.8 m) in height to induce rapid new growth for spring budwood.

*Branching habit.*—Low apical dominance allows numerous small branches to create a feathered condition throughout the tree.

*Productivity.*—Tree very productive, fruit has no commercial value.

*Bearer.*—Regular.

*Density.*—Dense. Numerous lateral branching increases density. Tree is cut back to 5 to 6 feet (1.5 to 1.8 m) in dormant season to promote rapid growth for desirable budwood.

*Hardiness.*—Hardy in all stone fruit growing areas in California.

Trunk:

*Size.*—Medium to large. Circumference 19 inches (48 cm) measured 9 inches (23 cm) above ground on a 7 year old tree. Varies slightly with soil type, climatic conditions and cultural practices.

*Surface texture.*—Medium shaggy. Roughness increases with age of tree.

*Color.*—Brown to soot brown (5-F-4) to (5-F-5).

Branches:

*Size.*—Medium. Average circumference 9 inches (23 cm), measured 58 inches (147 cm) above ground. Crotch angle approximately 30 degrees.

*Surface texture.*—New growth smooth. Mature growth medium rough.

*Lenticels*.—Medium to large. Average length — 1/8" (3.2 mm); Average width — 1/16" (1.6 mm); Color varies from grayish orange to golden yellow (5-B-6) to (5-B-8); Numerous — 31 in 4 square inch (26 sq. cm) surface.

*Color*.—New growth varies from olive brown (4-D-6) on under side to violet brown on upper side exposed to sun; Mature growth varies from light brown to hair brown (5-D-5) to (5-E-5).

Leaves:

*Size*.—Small; Average length — 1¾ inches (4.4 cm); Average width — 7/8 inch (2.2 cm).

*Form*.—Ovate.

*Apex*.—Acuminate.

*Base*.—Obtuse.

*Margin*.—Double serrate.

*Thickness*.—Medium.

*Surface texture*.—Upper surface relatively smooth, only slightly indented on upper surface over leaf vein; Lower surface relatively smooth, midrib with pinnate veining create small ridges.

*Petiole*.—Color — grayish yellow (2-B-4); Average length — 19/64 inch (7.5 mm); Average width — 3/64 inch (1.2 mm).

*Color*.—Upper surface — green to dark green (27-F-6) to (27-F-8). Lower surface — light green to jade green (27-E-5) to (27-E-7).

*Midvein*.—Pronounced; Midvein same width as petiole for approximately ½ of leaf; Color — grayish yellow (2-B-4); Venation — pinnate.

*Glands*.—Eglandular.

Flowers buds:

*Quantity per spur*.—Average quantity 6, varies from 1 to 12.

*Size*.—Small. Average length — 21/64 inch (8.3 mm). Average diameter — 13/64 inch (5.2 mm).

*Hardiness*.—Hardy in all stone fruit growing areas of California. Grown in Zone 9.

*Form*.—Plump, free; Varies from conic to elongated as bud development progresses.

*Color*.—White (1-A-1).

*Pedicel*.—Average length — 29/64 inch (11.5 mm). Average width — 3/64 inch (1.2 mm). Color — grayish green (1-D-5).

Flowers:

*Development*.—Perigynous, complete, single pistol, multiple stamens, five petals and sepals alternately arranged.

*Size*.—Small. Average height — 21/64 inch (8.3 mm). Average diameter — 55/64 inch (21.8 mm).

*Color*.—White (1-A-1).

*Pistil*.—Usually one. Average length — 5/16 inch (7.9 mm). Color — white (1-A-1).

*Stamens*.—28 to 31 per flower. Average filament length — ¼ inch (6.4 mm). Color — white (1-A-1). Average stamen length — 17/64 inch (6.7 mm), same height as pistils in mature flower. Anther color — light yellow to yellow (4-A-5) to (4-A-6).

*Petals*.—Quantity — five, alternately arranged to sepals. Shape — obovate, narrows at point of attachment. Size — medium. Average length — 23/64 inch (9.1 mm). Average width — 19/64 inch (7.5 mm). Surface edges vary from smooth to slightly scalloped. Color — white (1-A-1).

*Sepals*.—Quantity — five, alternately arranged to petals. Glabrous. Shape — ovate, somewhat triangular, tip rounded. Average length — 5/32 inch (4.0 mm). Average width at base — 3/32 inch (2.4 mm). Color — brownish red (10-D-7) on lower center to grayish green (1-D-5) along outer edges.

*Pollen*.—Abundant. Unknown as to self-fertility. Unimportant as to value of interstock.

*Fragrance*.—Very slight.

*Blooming period*.—Date of first bloom Feb. 27, 2000. Date of last bloom Mar. 7, 2000. Varies slightly with climatic conditions.

Flower stem:

*Size*.—Medium. Average length — 15/64 inches (6.0 mm). Average width — 3/64 inch (1.2 mm).

*Color*.—Grayish yellow (2-C-4).

Fruit:

*Maturity when described*.—Firm ripe, no commercial value.

*Date of fruit ripening*.—Jun. 22, 1999. Fruit drops on ground, no commercial value.

*Form*.—Globose, slightly elongated.

*Size*.—Small. Average diameter axially 15/16 to 1 inch (23.8 to 25.4 mm). Average transversely in suture plane ¾ to 15/16 inch (19.0 to 23.8 mm). Average weight 7.9 grams. Average weight varies with quantity of fruit per tree, fertility of soil and climatic conditions.

*Suture*.—Smooth. Extends from base to apex.

*Ventral surface*.—Rounded, smooth.

*Apex*.—Slight, rounded.

*Base*.—Flat, varies from flat to slightly retuse.

*Cavity*.—Rounded. Very slightly elongated in suture plane. Average depth — 1/16 inch (1.6 mm). Average breadth — 1/8 inch (3.2 mm).

Stem:

*Size*.—Small. Average length — 3/8 inch (9.5 mm). Average width — 1/16 inch (1.6 mm).

*Color*.—Grayish green to spring green (30-C-6) to (30-C-7).

Flesh:

*Ripens*.—Even.

*Texture*.—Firm.

*Fibers*.—None.

*Aroma*.—Slight.

*Eating quality*.—Poor, no commercial value.

*Flavor*.—Acid.

*Juice*.—Moderate.

*Color*.—Pale yellow to butter yellow (4-A-4) to (4-A-5). Pit cavity color — golden yellow (4-B-5).

Skin:

*Color*.—Yellow to amber yellow (4-A-6) to (4-B-6).

*Thickness*.—Medium.

*Texture*.—Medium.

*Bloom*.—Moderate.

*Tendency to crack*.—Slight in wet weather.

*Tenacity*.—Tenacious to flesh.

Stone:

*Type*.—Clingstone.

*Size*.—Small. Average length 35/64 inch (13.9 mm). Average width 25/64 inch (9.9 mm). Average thickness — 17/64 inch (6.8 mm).

*Form*.—Ovoid.

*Base*.—Usually round. Varies from rounded to straight.

*Apex*.—Acuminate. Length — short, 1/16 inch (1.6 mm).

*Surface*.—Pitted throughout. Pits small and relatively uniform. One very shallow groove on each side of suture.

*Sides*.—Equal.

*Tendency to split*.—None.

*Color*.—Light brown to oak brown (5-C-5) to (5-D-5) when dry.

Use: Rootstock interstock for tree size control with cherries (*Prunus avium*).

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics, with abnormal fungus, bacterial, virus, or insect susceptibility is destroyed and eliminated from our breeding program.

The present new variety of Myrobalan tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of Myrobalan (*Prunus cerasifera*) tree, substantially as illustrated and described, characterized by being medium to large in size, moderately vigorous, upright growth and having graft compatibility with numerous rootstocks and also with various cherry trees, giving this Myrobalan tree the potential to be used as an interstock for growing cherries on various non-compatible rootstocks; the new variety is further characterized by having the ability to reduce the size of the cherry tree by shortening the length of the interstock between the cherry scion and the rootstock.

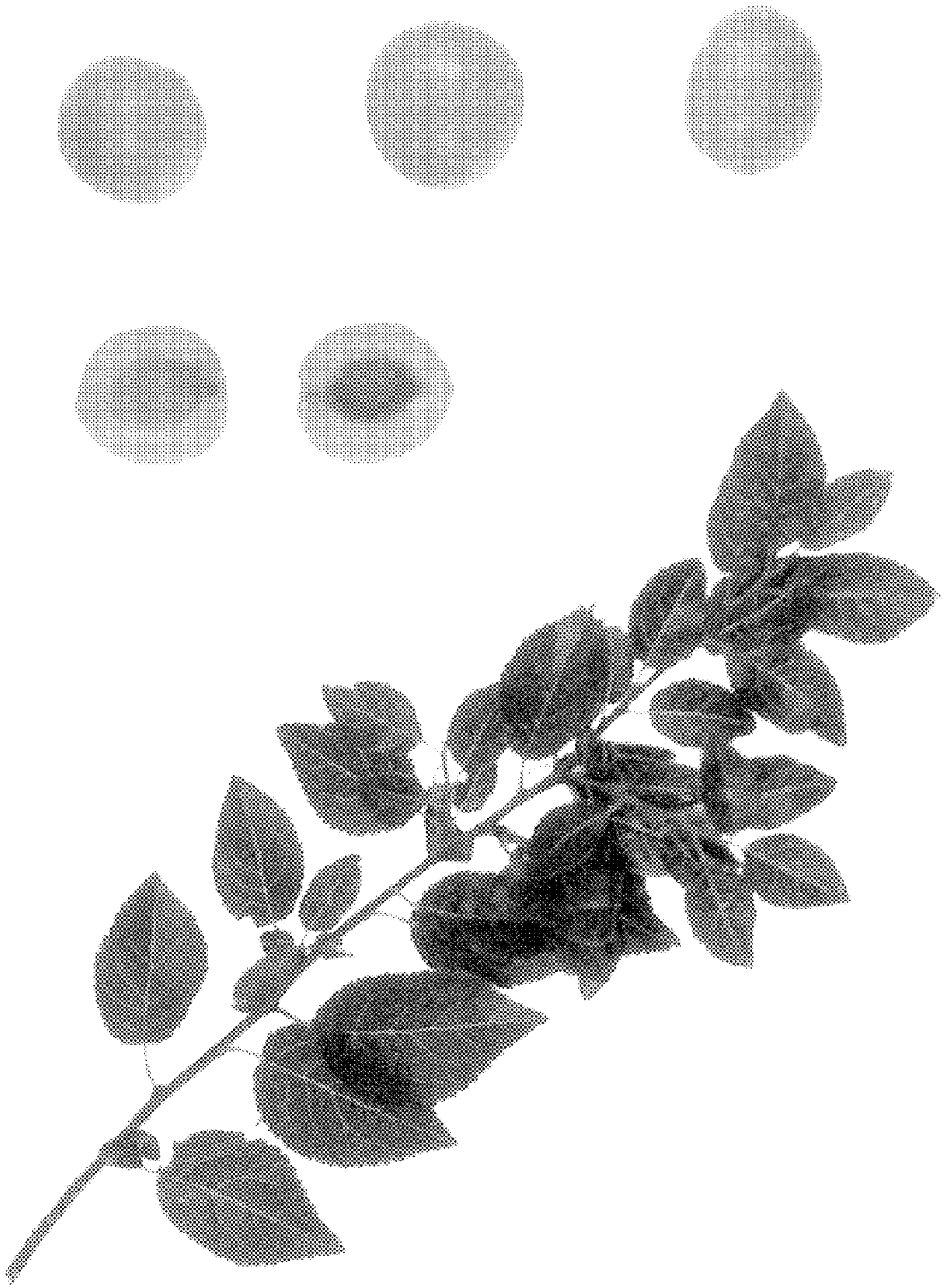

* * * * *